US007954495B2

(12) United States Patent
Joung

(10) Patent No.: US 7,954,495 B2
(45) Date of Patent: Jun. 7, 2011

(54) DUSTPROOF MASK FOR NOSE

(76) Inventor: Jin Gu Joung, Seoul (KR)

( * ) Notice: Subject to any disclaimer, the term of this patent is extended or adjusted under 35 U.S.C. 154(b) by 166 days.

(21) Appl. No.: 12/084,105

(22) PCT Filed: Apr. 12, 2007

(86) PCT No.: PCT/KR2007/001778
§ 371 (c)(1),
(2), (4) Date: Apr. 25, 2008

(87) PCT Pub. No.: WO2007/139814
PCT Pub. Date: Nov. 15, 2007

(65) Prior Publication Data

US 2009/0151732 A1 Jun. 18, 2009

(30) Foreign Application Priority Data

May 10, 2006 (KR) ........................ 10-2006-0041981

(51) Int. Cl.
*A61F 9/00* (2006.01)

(52) U.S. Cl. ........................................................ 128/858

(58) Field of Classification Search .................. 128/858, 128/206.11; 606/199, 204.45; D24/106
See application file for complete search history.

(56) References Cited

U.S. PATENT DOCUMENTS

| | | | | | |
|---|---|---|---|---|---|
| 2,274,997 | A | * | 3/1942 | Thurman | 128/858 |
| 3,463,149 | A | * | 8/1969 | Albu | 128/204.12 |
| 4,221,217 | A | * | 9/1980 | Amezcua | 128/206.11 |
| 6,971,388 | B1 | * | 12/2005 | Michaels | 128/206.11 |

* cited by examiner

*Primary Examiner* — Patricia M Bianco
*Assistant Examiner* — Camtu T Nguyen
(74) *Attorney, Agent, or Firm* — Bacon & Thomas, PLLC

(57) ABSTRACT

Disclosed is a dustproof mask for nose, in which filters are inserted into the nasal cavities of a user. The dustproof mask for nose includes a clamping unit having two wings and surrounding the nasal septum (the septum of the nose) of a user; connection portions installed at tips of the two wings; and filters installed at the connection portions. In the dustproof mask for nose, the filters (10) have a hemispheric shape, nipple-shaped connectors, which are formed at the connection portions, are inserted into connection holes, which are formed through the central areas of the filters, and fixing protrusions for firmly holding the nasal septum are formed on the wings of the clamping unit.

2 Claims, 4 Drawing Sheets

DUSTPROOF MASK FOR NOSE

TECHNICAL FIELD

The present invention relates to a dustproof mask for a nose, in which filters are inserted into the nasal cavities of a user so as to filter out dust from air flowing into the nasal cavities.

BACKGROUND ART

The inventor of the present invention already provided a dustproof mask for a nose (disclosed in published Korean Patent Application No. 10-2005-0073967), which includes a clamping unit surrounding the nasal septum (the septum of the nose) of a user, filter receiving units connected to the clamping unit, and filters respectively installed on the filter receiving units, so that the filter receiving units are attached closely to the inner walls of the nasal cavities of the user. The filters are installed at portions of the filter receiving units having the maximum diameter. In the above dustproof mask for a nose, when the clamping unit is fixed to the nasal septum, the filter receiving units formed at both tips of the clamping unit are inserted into the nasal cavities and the filters installed on the filter receiving units filter out dust from air flowing into the nasal cavities.

Korean Patent Laid-open Publication No. 10-2005-0008729 discloses a nose mask, in which double filters are installed at tips of an installation shaft and cellulose sponges are arranged in the double filters. The nose mask includes the double filters, which have an approximately flat board shape, thereby causing difficulty in circulating air and thus causing inconvenience for breathing through the nose to a user. Further, the structure for installing the double filters at the tips of the installation shaft is complicated, thus increasing the production cost of the nose mask.

Japanese Patent Laid-open Publication No. H08-71170 discloses a dustproof means for a nose. Projecting parts are formed on fixing parts of a connecting piece of the mask so that the means is not separated from the nose of a user even when a strong extrusion force, such as sneezing, is applied to the means. However, filters fill the front ends of the nasal cavities having a comparatively small diameter and have a flat board shape, thereby having a small surface area and thus causing inconvenience for breathing through the nose to the user.

Further, Japanese Patent Laid-open Publication No. H11-137702 discloses a nose mask, in which the surface area of the filters is increased so as to give a user convenience for breathing through the nose. However, the filters have a hollow semi-ellipsoidal shape such that the diameter of the middle portion of a main body of each of the filters is the same as that of the front end of the main body of each of the filters. In the above nose mask, since the diameter of the main wall of each of the filters cannot coincide with the inner diameter of the nasal cavity of a user, non-filtered air may be inhaled through gaps between the filters and the nasal cavities during breathing. Further, the nose mask does not include any unit for holding the mask in the nose, and thus may be separated from the nose due to sneezing.

Accordingly, the inventor provided a dustproof mask for nose disclosed in Korean Patent Application No. 10-2005-0125179. In the mask, nipple-shaped connectors are formed at tips of a clamping unit and filters are installed directly on the connectors so that the filters are located in the nasal cavities of a user, thus giving the user convenience for breathing through the nose. However, the mask is disadvantageous in that the filters installed at the tips of the clamping unit have an approximately flat board shape and thus have a comparatively small surface area. Further, the mask is disadvantageous in that the clamping unit has an insufficient force for holding the nasal septum.

TECHNICAL PROBLEM

Therefore, the present invention has been made in view of the above problems, and it is an object of the present invention to provide a dustproof mask for a nose, as disclosed in Korean Patent Application No. 10-2005-0125179, in which filters provided with extension portions in the form of an umbrella at the edges thereof have an approximately hemispheric shape, such that the extension portions contact closely the inner walls of the nasal cavities of a user so as to permit a difference between the diameters of the filters and the inner diameters of the nasal cavities and are bent in exhalation so as to provide convenience in exhalation to the user, in combination with Japanese Patent Laid-open Publication No. H11-137702 for increasing the surface areas of filters, tips of a clamping unit are inserted into the central areas of the filters, in combination with Korean Patent Laid-open Publication No. 10-2005-0008729, and the clamping unit firmly holds the nasal septum, in combination with Japanese Patent Laid-open Publication No. H8-71170 and Korean Patent Laid-open Publication No. 10-2605-0008729.

TECHNICAL SOLUTIONS AND SUMMARY

In accordance with an aspect of the present invention, the above and other objects can be accomplished by the provision of a dustproof mask for a nose comprising a clamping unit having two wings and surrounding the nasal septum (the septum of the nose) of a user; connection portions installed at tips of the two wings; and filters installed at the connection portions, wherein the filters have a hemispheric shape, nipple-shaped connectors, which are formed at the connection portions, are inserted into connection holes, which are formed through the filters, and fixing protrusions are formed on the wings of the clamping unit.

Preferably, extension portions are formed at the edges of front ends of the hemispheric filters.

ADVANTAGEOUS EFFECTS

The present invention provides a dustproof mask for nose, in which respects instructed by several publicly known inventions disclosed in the previous applications are optimally combined, such that the mask is not easily separated from the nose of a user due to an extrusion force in exhalation, such as sneezing, filters having a hemispheric shape are installed in the broadest areas in the nasal cavities so as to increase the surface areas of the filters, extension portions are formed at the edges of the hemispheric filters so as to permit a difference between the diameters of the filters and the inner diameters of the nasal cavities and are bent in exhalation so as to provide convenience in exhalation to the user, and nipple-shaped connectors connect the filters to wings of a clamping unit so as to facilitate the connection of the filters and the wings to reduce the production cost of the mask.

BRIEF DESCRIPTION OF THE DRAWINGS

The above and other objects, features and other advantages of the present invention will be more clearly understood from the following detailed description taken in conjunction with the accompanying drawings, in which.

DETAILED DISCUSSION IN CONJUNCTION WITH THE DRAWINGS

Figure 1:
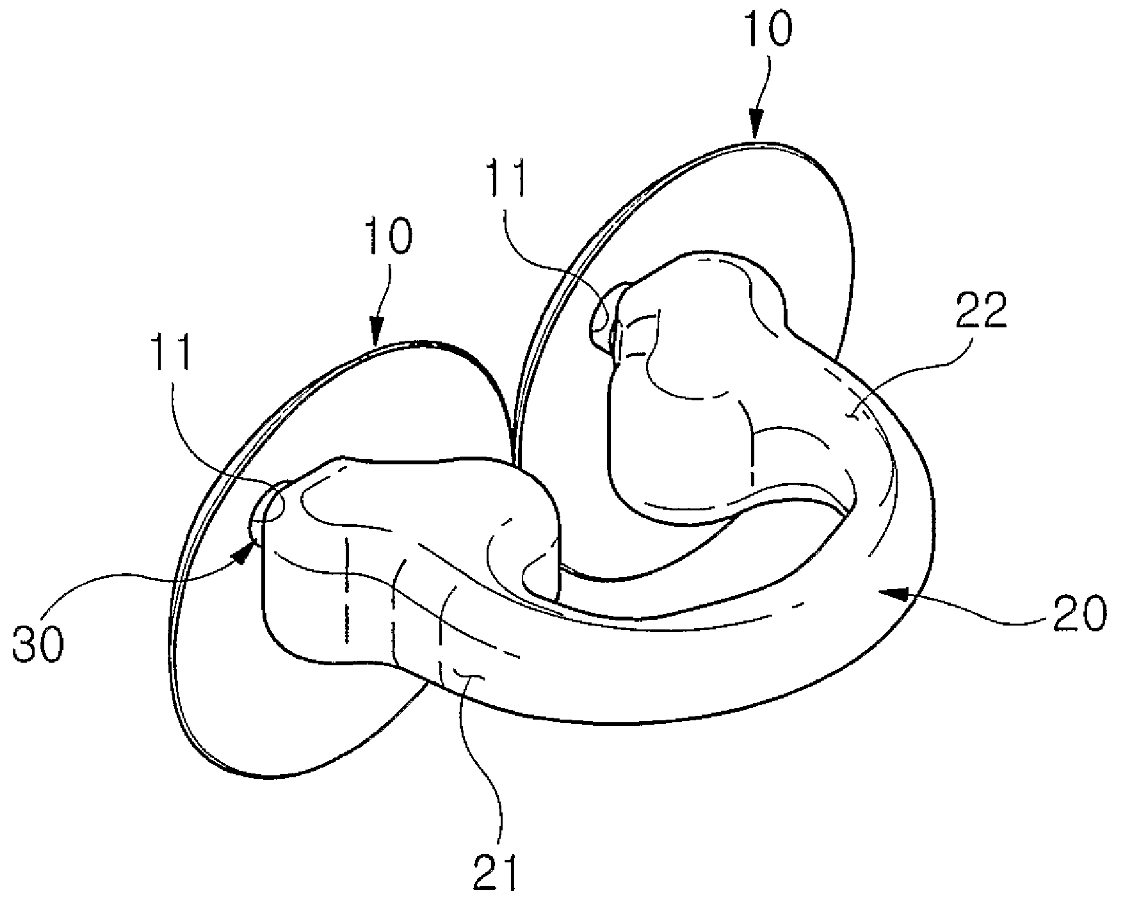
FIG. 1 is a perspective view of a dustproof mask for nose in accordance with one embodiment of the present invention.
Figure 2:
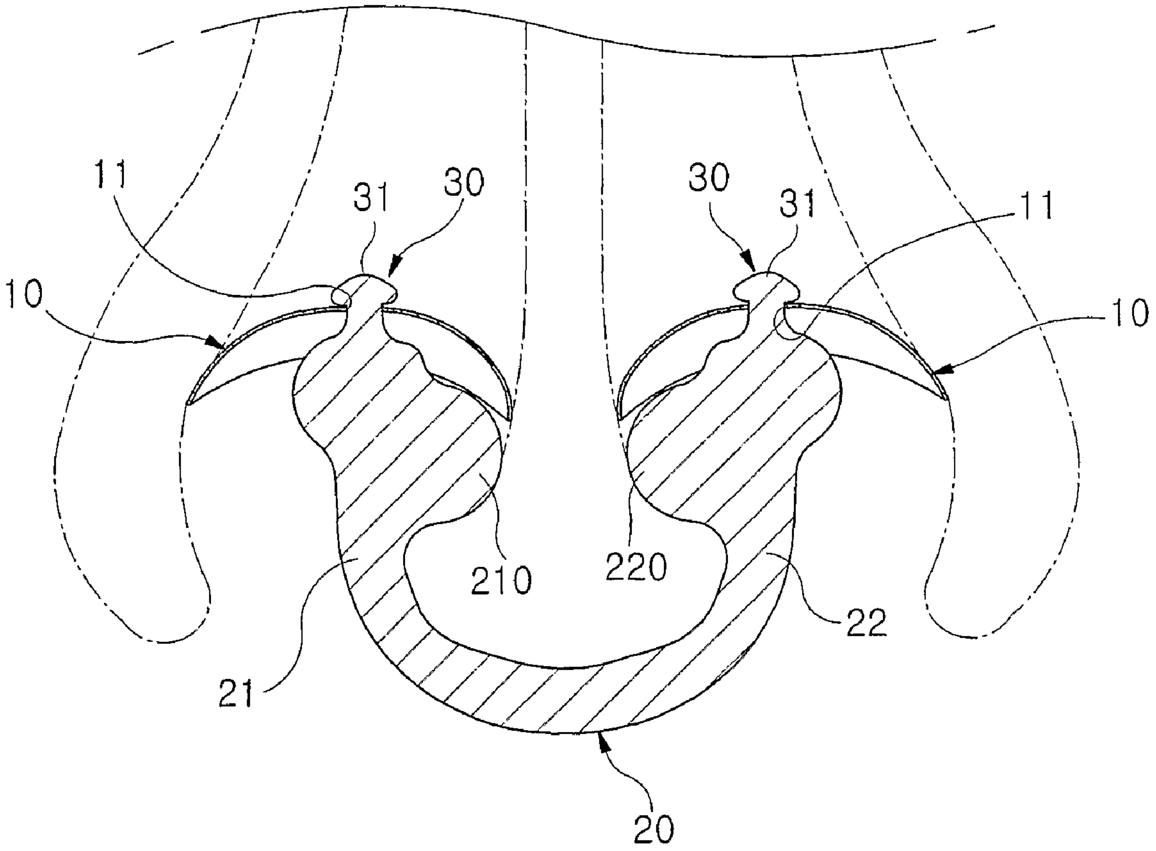
FIG. 2 is a sectional view of the dustproof mask for nose of FIG. 1 in a used state.

FIG. 1 is a perspective view of a dustproof mask for nose in accordance with one embodiment of the present invention.

A dustproof mask for a nose of the present invention includes a clamping unit 20 having two wings 21 and 22 and surrounding the nasal septum (the septum of the nose) of a user, connection portions 30 installed at the tips of the two wings 21 and 22, and filters 10 installed at the connection portions 30, as disclosed in Korean Patent Application No. 10-2005-0125179 filed by the inventor of the present invention.

First, the dustproof mask for a nose of the present invention, as developed from the technique disclosed in Japanese Patent Laid-open Publication No. H11-137702 for increasing the surface areas of filters, is characterized in that the filters 10 have an approximately hemispheric shape such that extension portions 101 having the shape of an umbrella are formed at the edges of the filters 10. The extension portions 101 of the filters 10 contact closely the inner walls of the nasal cavities so as to narrow the diameters of the circumferences of the filters 10, and thus a difference between the diameters of the filters 10 and the inner diameters of the nasal cavities is permitted. Further, during exhalation, the extension portions 101 are bent, and thus provide convenience in exhalation to the user.

Figure 3:
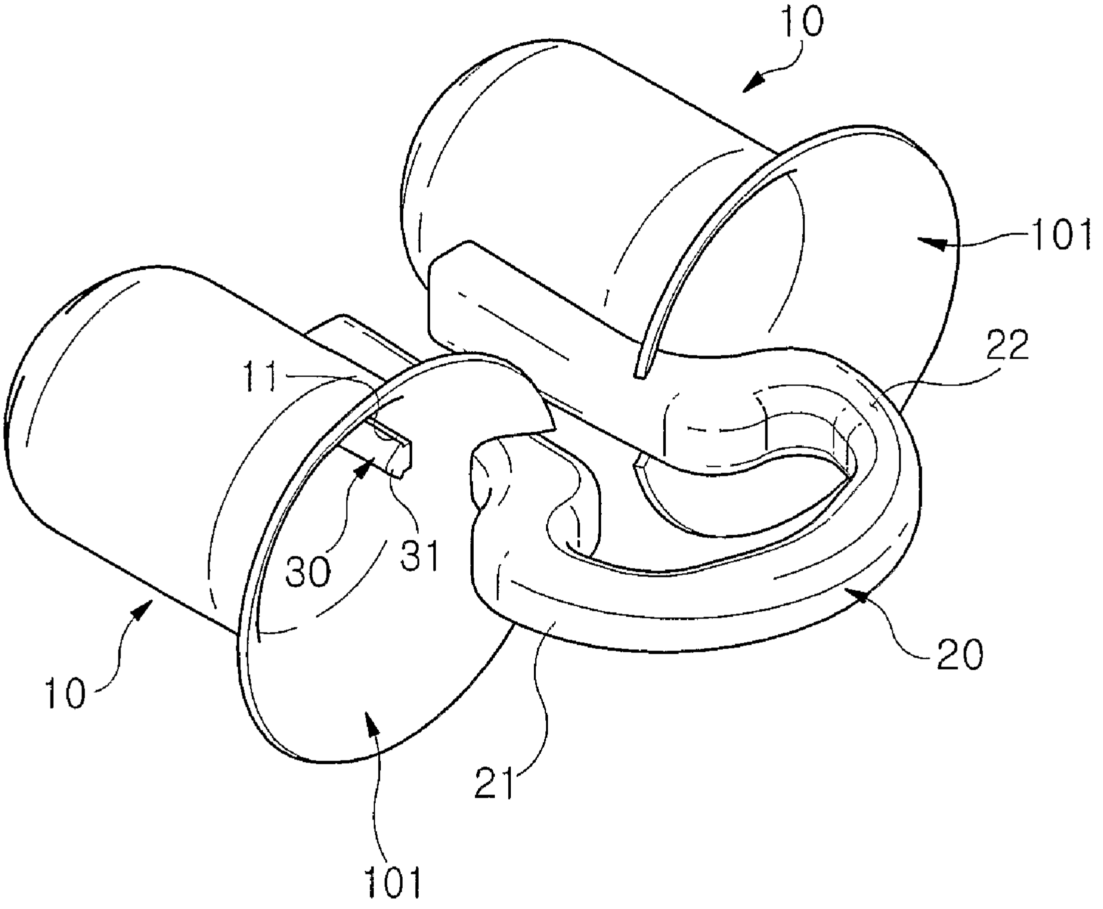
FIG. 3 is a perspective view of a dustproof mask for nose in accordance with another embodiment of the present invention.

Second, the dustproof mask for a nose of the present invention, as developed from the technique disclosed in Korean Patent Laid-open Publication No. 10-2005-0008729, is characterized in that the filters 10 are connected to the two wings 21 and 22 of the clamping unit 20 such that the central concave portions of the filters 10 are located at the central areas of the nasal cavities of the user. As improvement of the technique disclosed in Korean Patent Laid-open Publication No. 10-2005-0008729, it is preferable that the filters 10 are connected to the two wings 21 and 22 of the clamping unit 20 by inserting nipple-shaped connectors 31, which are formed at the connection portions 30 installed at the two wings 21 and 22 of the clamping unit 20, into connection holes 11, which are formed through the central areas of the filters 10. However, the filters 10 may be connected to the two wings 21 and 22 of the clamping unit 20 by inserting the nipple-shaped connectors 31 into holes, which are formed through the side walls of the filters 10, as shown in FIG. 3.

Figure 4:
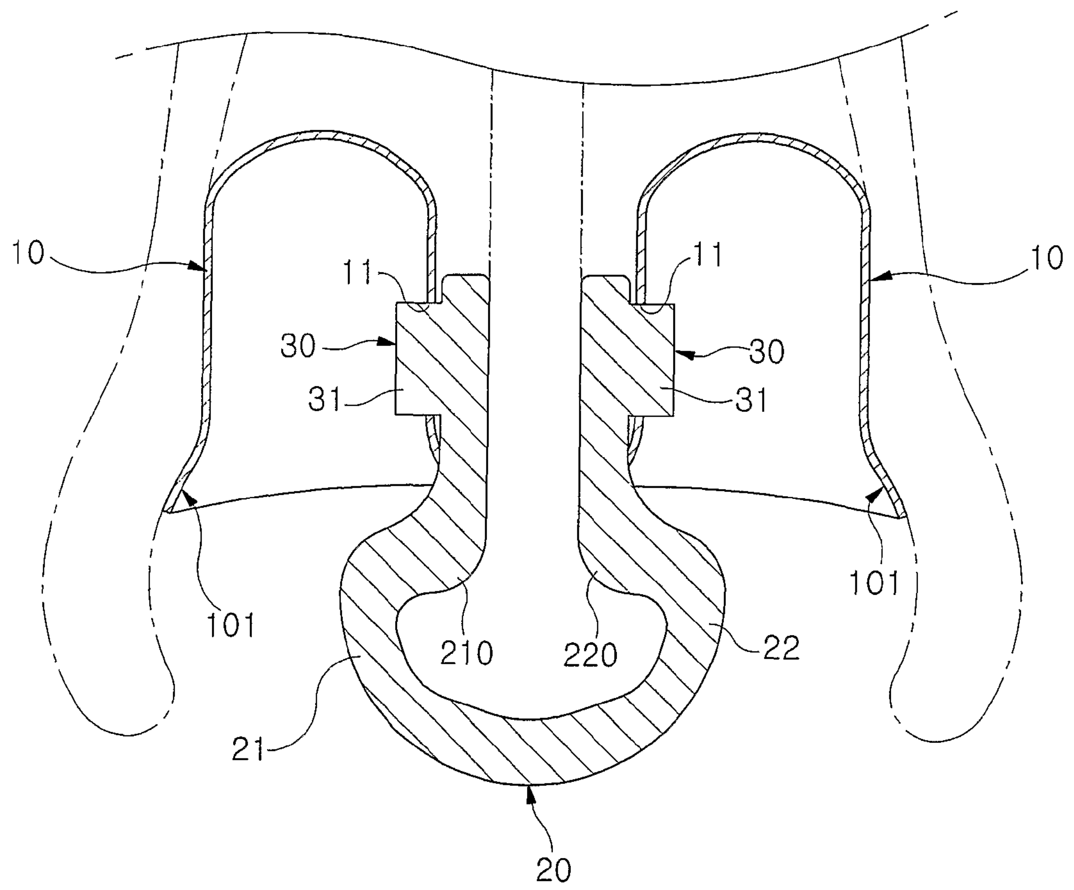
FIG. 4 is a sectional view of the dustproof mask for nose of FIG. 3 in a used state.

Third, the dustproof mask for a nose of the present invention, in combination with the techniques disclosed in Japanese Patent Laid-open Publication No. H8-71170 and Korean Patent Laid-open Publication No. 10-2005-0008729 for firmly holding a clamping unit onto the nasal septum of a user, is characterized in that fixing protrusions 210 and 220 are formed on the wings 21 and 22 of the clamping unit 20 as seen in FIG. 4.

INDUSTRIAL APPLICABILITY

As apparent from the above description, the present invention provides a dustproof mask for a nose, in which respects instructed by several publicly known inventions disclosed in the previous applications are optimally combined, such that the mask is not easily separated from the nose of a user due to extrusion force in exhalation, such as sneezing, filters having a hemispheric shape are installed in the broadest areas in the nasal cavities so as to increase the surface areas of the filters, extension portions are formed at the edges of the hemispheric filters so as to permit a difference between the diameters of the filters and the inner diameters of the nasal cavities and are bent in exhalation so as to provide convenience in exhalation to the user, and nipple-shaped connectors connect the filters to wings of a clamping unit so as to facilitate the connection of the filters and the wings to reduce the production cost of the mask.

Although the preferred embodiments of the present invention have been disclosed for illustrative purposes, those skilled in the art will appreciate that various modifications, additions and substitutions are possible, without departing from the scope and spirit of the invention as disclosed in the accompanying claims.

The invention claimed is:

1. A dustproof mask for a nose, comprising:

a clamping unit having two wings and surrounding the nasal septum of a user, each wing defining a tip;

a connection portion installed at said tip of each of said two wings; and hemispherically-shaped filters installed at the connection portions, wherein:

each connection portion includes a nipple-shaped connector, which is formed at the end of each connection portions and which is inserted each of through the filters, and fixing protrusions formed on said wings of the clamping unit.

2. The dustproof mask for a nose according to claim 1, wherein:

said fixing protrusions extend outwardly from their respective wings.

* * * * *